US009611201B2

(12) United States Patent
De Lombaert et al.

(10) Patent No.: US 9,611,201 B2
(45) Date of Patent: Apr. 4, 2017

(54) PROCESSES FOR PREPARING (R)-1-(5-CHLORO-[1,1'-BIPHENYL]-2-YL)-2,2,2-TRIFLUOROETHANOL AND 1-(5-CHLORO-[1,1'-BIPHENYL]-2-YL)-2,2,2-TRIFLUOROETHANONE

(71) Applicant: Karos Pharmaceuticals, Inc., New Haven, CT (US)

(72) Inventors: Stéphane De Lombaert, Brisbane, CA (US); Daniel R. Goldberg, Redding, CT (US)

(73) Assignee: Karos Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 15/059,627

(22) Filed: Mar. 3, 2016

(65) Prior Publication Data
US 2016/0257633 A1 Sep. 8, 2016

Related U.S. Application Data

(60) Provisional application No. 62/128,652, filed on Mar. 5, 2015.

(51) Int. Cl.
C07C 29/32 (2006.01)
C07C 29/143 (2006.01)
C07C 259/10 (2006.01)
C07C 45/45 (2006.01)
C07C 49/80 (2006.01)

(52) U.S. Cl.
CPC ............ *C07C 29/32* (2013.01); *C07C 29/143* (2013.01); *C07C 45/455* (2013.01); *C07C 49/80* (2013.01); *C07C 259/10* (2013.01); C07B 2200/07 (2013.01)

(58) Field of Classification Search
None
See application file for complete search history.

(56) References Cited

U.S. PATENT DOCUMENTS

| 5,380,927 | A | 1/1995 | Paradies |
| 9,199,994 | B2 | 12/2015 | De Lombaert et al. |
| 2010/0087431 | A1* | 4/2010 | Brooks ............... C07D 409/14 514/233.5 |
| 2010/0331294 | A1 | 12/2010 | Black et al. |
| 2012/0101281 | A1 | 4/2012 | Murugesan et al. |
| 2013/0102611 | A1 | 4/2013 | Charlton et al. |
| 2015/0080393 | A1 | 3/2015 | De Lombaert et al. |
| 2016/0096836 | A1 | 4/2016 | De Lombaert et al. |

FOREIGN PATENT DOCUMENTS

| CN | 101591332 | 12/2009 |
| CN | 104045626 | 9/2014 |
| EP | 3061761 | 8/2016 |
| WO | WO98/08850 | 3/1998 |
| WO | WO01/66531 | 9/2001 |
| WO | WO03/051841 | 6/2003 |
| WO | WO03/051842 | 6/2003 |
| WO | WO2004/035550 | 4/2004 |
| WO | WO2004/111004 | 12/2004 |
| WO | WO2004/111031 | 12/2004 |
| WO | WO2005/073199 | 11/2005 |
| WO | WO2006/074957 | 7/2006 |
| WO | WO2007/089335 | 8/2007 |
| WO | WO2008/073933 | 6/2008 |
| WO | WO2008/100412 | 8/2008 |
| WO | WO2009/009561 | 1/2009 |
| WO | WO2009/014972 | 1/2009 |
| WO | WO2009/040075 | 4/2009 |
| WO | WO2009/123978 | 10/2009 |
| WO | WO2010/046109 | 4/2010 |
| WO | WO2010/056992 | 5/2010 |
| WO | WO2010/065333 | 6/2010 |
| WO | WO2010/147094 | 12/2010 |
| WO | WO2011/053977 | 5/2011 |
| WO | WO2011/056916 | 5/2011 |
| WO | WO2011/063181 | 5/2011 |
| WO | WO2011/100285 | 8/2011 |
| WO | WO2011/103196 | 8/2011 |
| WO | WO2012/048222 | 4/2012 |
| WO | WO2012/061576 | 5/2012 |
| WO | WO2013/030802 | 3/2013 |
| WO | WO2013/059146 | 4/2013 |
| WO | WO2013/074889 | 5/2013 |
| WO | WO2013/105057 | 7/2013 |
| WO | WO2013/105058 | 7/2013 |
| WO | WO2013/105061 | 7/2013 |
| WO | WO2013/105063 | 7/2013 |
| WO | WO2013/105065 | 7/2013 |
| WO | WO2013/105066 | 7/2013 |

(Continued)

OTHER PUBLICATIONS

Cheng et al. / Tetrahedron Letters 54 (2013) 4483-4486.*
Abid et al., "Inhibition of gut- and lung derived serotonin attenuates pulmonary hypertension in mice," Am. J. Physiol Lung Cell Mol Physiol, Jul. 2012, 303:L500-L508.
Alpini et al. "Serotonin metabolism is dysregulated in cholangiocarcinoma, which has implications for tumor growth," Cancer Res., Nov. 2008, 68:9184-9193.
Antic et al., "Treating skin and lung fibrosis in systemic sclerosis: a future filled with promise?" Current Opinion in Phammacology, 2013, 13:455-462.
Artlett, "Animal models of scleroderma: fresh insights." Curr. Opin. Rheumatol., 2010, 22:677-682.
Ban et al., "Impact of Increased Plasma Serotonin Levels and Carotid Atherosclerosis on Vascular Dementia," Atherosclerosis, 2007, 195, 153-159.

(Continued)

*Primary Examiner* — Sudhakar Katakam
*Assistant Examiner* — Ana Z Muresan
(74) *Attorney, Agent, or Firm* — Fish & Richardson P.C.

(57) ABSTRACT

The present invention relates to processes for the preparation of (R)-1-(5-chloro-[1,1'-biphenyl]-2-yl)-2,2,2-trifluoroethanol, 1-(5-chloro-[1,1'-biphenyl]-2-yl)-2,2,2-trifluoroethanone, and intermediates thereof, which are useful in the preparation of inhibitors of TPH1 for the treatment of, for example, gastrointestinal, cardiovascular, pulmonary, inflammatory, metabolic, low bone mass diseases, serotonin syndrome, and cancer.

11 Claims, No Drawings

(56) References Cited

FOREIGN PATENT DOCUMENTS

| WO | WO2013/111110 | 8/2013 |
|---|---|---|
| WO | WO2013/148978 | 10/2013 |
| WO | WO2014/082034 | 5/2014 |
| WO | WO2014/124523 | 8/2014 |
| WO | WO2014/195847 | 12/2014 |
| WO | WO2015/075023 | 5/2015 |
| WO | WO2015/075025 | 5/2015 |
| WO | WO2015/089137 | 6/2015 |
| WO | WO2016/177690 | 11/2016 |

OTHER PUBLICATIONS

Berge et al., "Pharmaceutical Salts," J. Pharm. Sci., 1977, 66(1):1-19.
Brown et al., "The tryptophan hydroxylase inhibitor LX1031 shows clinical benefit in patients with nonconstipating irritable bowel syndrome," Gastroenterology, 2011, 141:507-516.
Camilleri, "LX-1031, A Tryptophan 5-hydroxylase Inhibitor, and Its Potential in Chronic Diarrhea Associated With Increased Serotonin," Neurogastroenterol Motil., Mar. 2011, 23(3):193-200.
Cheng et al., Tetrahedron Letters, 54, 2013, pp. 4483-4486.
Cianchetta et al., "Mechanism of Inhibition of Novel Tryptophan Hydroxylase Inhibitors Revealed by Co-crystal Structures and Kinetic Analysis," Current chemical genomics, 2010, 4:19-26.
Coleiro et al., "Treatment of Raynaud's phenomenon with the selective serotonin reuptake inhibitor fluoxetine," Rheumatology, Sep. 2001 40(9):1038-1043.
Corey and Link, "A General, Catalytic, and Enantioselective Synthesis of Alpha-amino Acids," J. Am. Chem. Soc., 1992, 114:1906-1908.
Costedio et al., "Serotonin and Its Role in Colonic Function and in Gastrointestinal Disorders," Diseases of the Colon and Rectum, Mar. 2007, 50(3): 376-88.
Crowell, "Role of Serotonin in the Pathophysiology of the Irritable Bowel Syndrome," British Journal of Pharmacology, 2004, 141:1285-93.
Dale and Mosher, "Nuclear Magnetic Resonance Enantiomer Regents. Configurational Correlations Via Nuclear Magnetic Resonance Chemical Shifts of Diastereomeric Mandelate, O-Methylmandelate, and alpha-Methoxy alpha-Trifluoromethylphenylacetate (MTPA) Esters," J. Am. Chem. Soc., Jan. 1973, 95(2):512-519.
Dees et al., "Platelet-derived serotonin links vascular disease and tissue fibrosis," J. Exp. Med., Apr. 2011, 208(5):961-972.
DeGraw et al., "Experimentally Induced Phenylketonuria I. Inhibitors of Phenylalanine Hydroxylase," Life Sci., Jan. 1967, 10:64-66.
Derrett-Smith et al. "Animal models of scleroderma: lessons from transgenic and knockout mice." Curr. Opin. Rheumatol., 2009, 21:630-635.
Duerschmied et al., "Platelet Serotonin Promotes the Recruitment of Neutrophils to Sites of Acute Inflammation in Mice," Blood, Feb. 2013, 121(6):1008-1015.
Dürk et al., "Production of serotonin by tryptophan hydroxylase 1 and release via platelets contribute to allergic airway inflammation " Am J Respir Crit Care Med., Jan. 2013, 187(5): 476-485.
Ebrahimkhani et al., "Stimulating Healthy Tissue Regeneration by Targeting the 5-HT2B Receptor in Chronic Liver Disease," Nature Medicine, 2011 17, 1668-1673.
Egermayer et al., "Role of Serotonin in the Pathogenesis of Acute and Chronic Pulmonary Hypertension," Thorax, 1999, 54:161-168.
Engelman et al, "Inhibition of Serotonin Synthesis by Parachlorophenylalanine in Patients With the Carcinoid Syndrome," The New England Journal of Medicine, Nov. 1967, 277:1103-1108.
Fabre et al., "Modulation of bleomycin-induced lung fibrosis by serotonin receptor antagonists in mice," Eur. Resp. Journal, 2008, 32(2):426-436.
Fernandez and Eickelberg, "New Cellular and Molecular Mechanisms of Lung Injury and Fibrosis in Idiopathic Pulmonary Fibrosis," Lancet, Aug. 2012, 380: 680-88.

Fox and Khattar, "Carcinoid Heart Disease: Presentation, Diagnosis, and Management," Heart, 2004, 90:1224-1228.
Galligan and Parkman, "Recent advances in understanding the role of serotonin in gastrointestinal motility and functional bowel disorders," Neurogastroenterol Motil., 2007, 19(Suppl.2):1-4.
Gershon and Tack, "The Serotonin Signaling System: From Basic Understanding to Drug Development for Functional GI Disorders," Gastroenterology, 2007, 132:397-414.
Ghia et al., "Serotonin has a key role in pathogenesis of experimental colitis," Gastroenterology, 2009, 137(5): 1649-1660.
Herrick, "The pathogenesis, diagnosis and treatment of Raynaud phenomenon," Rheumatology, Aug. 2012, 8:469-479.
Hicks, "Use of molecular targeted agents for the diagnosis, staging and therapy of neuroendocrine malignancy," Cancer Imaging, Oct. 2010, 10:S83-S91.
International Preliminary Report on Patentability in International Application No. PCT/US2014/054202, dated Mar. 8, 2016, 10 pages.
International Search Report and Written Opinion in International Application No. PCT/US2014/054202 dated Dec. 2, 2014, 14 pages.
Iredale, "Models of liver fibrosis: exploring the dynamic nature of inflammation and repair in a solid organ " J. Clin. Invest., Mar. 2007, 117(3):539-548.
Iwamoto and Distler, "Molecular targets for therapy in systemic sclerosis," Fibrogenesis and Tissue Repair, Jun. 2012, 5(Suppl 1): S19, 6 pages.
Jin et al., "Substituted 3-(4-(1,3,5-triazin-2-y1)-phenyl)-2-aminopropanoic Acids as Novel Tryptophan Hydroxylase Inhibitors," Bioorganic & Medicinal Chemistry Letters, 2009, 19:5229-5232.
Jithunsa et all., "Copper (II) chloride-mediated cyclization reaction of N-alkoxy-ortho-alkynylbenzamides," Organic Letters 13 (3): 518-521.
Johnson, "The role of transglutaminase in the rat subtotal nephrectomy model of renal fibrosis," J Clin Invest., Jun. 1997, 99(12):2950-2960.
Journal of Pharmaceutical Science, 66, 2 (1977).
Kay et al., "Pulmonary Hypertension Induced in Rats by Monocrotaline and Chronic Hypoxia is Reduced by p-Chlorophenylalanine," Respiration, 1985, 47:48-56.
King et al., "A phase 3 trial of Pirfenidone in patients with idiopathic pulmonary fibrosis," The New England Journal of Medicine, May 2014, 370(22):2083-2092.
Kode et al., "FOXO1 orchestrates the bone-suppressing function of gut-derived serotonin," J. Clinical Investigation, Jul. 2012, 14 pages.
Koizumi et al , "Inhibition of Phenylalanine Hydroxylase, a Pterin-requiring Monooxygenase by Oudenone and its Derivatives," J. Antibiotics, Apr. 1982, 35(4):458-462.
Konigshoff et al., "Increased expression of 5-hydroxytryptamine2A/B receptors in idiopathic pulmonary fibrosis: a rationale for therapeutic intervention," Thorax, 2010, 65(11):949-55.
Lacerda et al. "Local serotonin mediates cyclic strain-induced phenotype transformation, matrix degradation, and glycosaminoglycan synthesis in cultured sheep mitral valves," Am J Physiol Heart Circ Physiol, 2012, 302(10): H1983-H1990.
Lau et al., "The Role of Circulating Serotonin in the Development of Chronic Obstructive Pulmonary Disease," PloS One, Feb. 2012, 7(2):e31617, 7 pages.
Lesurtel et al., "Role of Serotonin in the Hepato-gastrointestinal Tract: An Old Molecule for New Perspectives," Cell. Mol. Life Sci., 2008 65:940-952.
Li et al., "Serotonin Activates Dendritic Cell Function in the Context of Gut Inflammation," The American Journal of Pathology, Feb. 2011, 178(2):662-671.
Liang et al., "Serotonin Promotes the Proliferation of Serum-deprived Hepatocellular Carcinoma Cells Via Upregulation of FOXO3a," Molecular Cancer, 2013, 12:14, 11 pages.
Liedtke et al., "Experimental liver fibrosis research: update on animal models, legal issues and translational aspects." Fibrogenesis & Tissue Repair, 2013, 6:19, 25 pages.

(56) References Cited

OTHER PUBLICATIONS

Liu et al., "Discovery and Characterization of Novel Tryptophan Hydroxylase Inhibitors That Selectively Inhibit Serotonin Synthesis in the Gastrointestinal Tract," J. Pharmacol. Exp. Ther, 2008, 325(1):47-55.
Mann and Oakley, "Serotonin paracrine signaling in tissue fibrosis," Biochimica et Biophysica Acta, 2013, 1832:905-910.
Manocha and Khan, "Serotonin and GI Disorders: An Update on Clinical and Experimental Studies," Clinical and Translational Gastroenterology, 2012, 3:e13, 6 pages.
Margolis et al., "Pharmacological Reduction of Mucosal but Not Neuronal Serotonin Opposes Inflammation in Mouse Intestine," Gut, Jun. 2013, 1-10 (with Supplemental Information).
Maurer and Distler, "Emerging targeted therapies in sleroderma lung and skin fibrosis," Best Practice & Research Clinical Rheumatology, 2011, 25:843-858.
Mawe and Hoffman, "Serotonin signaling in the gut—functions, dysfunctions and therapeutic targets," Gastroenterology & Hepatology, Aug. 2013, 10:473-486.
Mawe et al., "Review article: intestinal serotonin signaling in irritable bowel syndrome," Aliment Pharmacol Ther, 2006, 23:1067-1076.
Moeller et al., "The bleomycin animal model: a useful tool to investigate treatment options for idiopathic pulmonary fibrosis?" Int J Biochem Cell Biol, 2008, 40(3):362-382.
Mouratis and Aidinis, "Modeling pulmonary fibrosis with bleomycin," Current Opinion in Pulmonary Medicine, 2011, 17:355-361.
Nowak et al., "Tryptophan hydroxylase-1 regulates immune tolerance and inflammation," J Exper Med, 2012, 209(11):2127-2135.
Ouadid et al., "Serotonin Increases Calcium Current in Human Atrial Myocytes via the Newly Described 5-Hydroxytyptamine4 Receptors," Molecular Pharmacology, 1992, 41:346-351.
Ouyang et al., "Combined Structure-Based Pharmacophore and 3D-QSAR Studies on Phenylalanine Series Compounds as TPH1 Inhibitors," Int J Molecular Sci, 2012, 13:5348-5363.
Pai et al., "Altered serotonin physiology in human breast cancers favors paradoxical growth and cell survival," Nov. 2009, 11(6):1-17.
Reinhard et al., "A rapid and sensitive assay for Tyrosine-3-Monooxygenase based upon the release of 3H2O and adsorption of [3H]-Tyrosine by charcoal," Life Sciences, 1986, 39(23):2185-2189.
Remington's Pharmaceutical Sciences, 17th ed., Mack Publishing Company, Easton, Pa., 1985, p. 1418.
Richeldi et al., "Efficacy and Safety of Nintedanib in Idiopathic Pulmonary Fibrosis," New England Journal of Medicine, May 2014, 370(22):2071-2082.
Robiolio et al., "Carcinoid Heart Disease: Correlation of High Serotonin Levels with Valvular Abnormalities Detected by Cardiac Catheterization and Echocardiography," Circulation, 1995, 92:790-795.
Shi et al., "Modulation of Peripheral Serotonin Levels by Novel Tryptophan Hydroxylase Inhibitors for the Potential Treatment of Functional Gastrointestinal Disorders," J Med Chem, 2008, 51:3684-3687.
Shinka et al., "Serotonin synthesis and metabolism-related molecules in a human prostate cancer cell line," Oncology Letters, 2011, 2:211-215.
Sikander et al., "Role of serotonin in gastrointestinal motility and irritable bowel syndrome," Clinica Chimica Acta, 2009, 403:47-55.
Skurikhin et al., "Effect of Antiserotonin Drug on the Development of Lung Fibrosis and Blood System Reactions after Intratracheal Administration of Bleomycin," Cell Technologies to Biology and Medicine, Feb. 2012, 4:519-523.
Soll et al., "Serotonin Promotes Tumor Growth in Human Hepatocellular Cancer," Hepatology 2010, 51(4):1244-1254.
Stokes et al., "p-Ethynylphenylalanine. A Potent Inhibitor of Tryptophan Hydroxylase," J Neurology, 2000, 74(5):2067-2073.
Sumara et al., "Gut-derived Serotonin is a Multifunctional Determinant to Fasting Adaptation," Cell Metabolism, Nov. 2012, 16:1-13.
Thomas et al., "Targeting the serotonin pathway for the treatment of pulmonary arterial hypertension," Pharmacology and Therapeutics, 2013, 138:409-417.
Wacker et al., "Structural Features for Functional Selectivity at Serotonin Receptors," Science, May 2013, 340(6132):615-619.
Weber, "p-Chlorophenylalanine depletion of gastrointestinal 5-hydroxytryptamine," Biochem Pharmacol, 1970, 19:2169-2172.
Yadav et al., "Lrp5 Controls Bone Formation by Inhibiting Serotonin Synthesis in the Duodenum," Cell, Nov. 2008, 135:825-837.
Yadav et al., "Pharamacological inhibition of gut-derived serotonin synthesis is a potential bone anabolic treatment for osteoporosis," Nature Medicine, Feb. 2010, 1-14.
Zhong et al., "Molecular Dynamics Simulation of Tryptophan Hydroxylase-1: Binding Modes and Free Energy Analysis to Phenylalanine Derivative Inhibitors," Int. J Molecular Sci, May 2013, 14:9947-9962.
Zhu et al., "3D-QSAR study of pyrrolidine derivatives as matrix metalloproteinase-2 inhibitors," Med Chem Res, 2009, 18:683-701.

\* cited by examiner

PROCESSES FOR PREPARING (R)-1-(5-CHLORO-[1,1'-BIPHENYL]-2-YL)-2,2,2-TRIFLUOROETHANOL AND 1-(5-CHLORO-[1,1'-BIPHENYL]-2-YL)-2,2,2-TRIFLUOROETHANONE

FIELD OF THE INVENTION

The present invention relates to processes for the preparation of (R)-1-(5-chloro-[1,1'-biphenyl]-2-yl)-2,2,2-trifluoroethanol, 1-(5-chloro-[1,1'-biphenyl]-2-yl)-2,2,2-trifluoroethanone, and intermediates thereof, which are useful in the synthesis of inhibitors of TPH1 for the treatment of, for example, gastrointestinal, cardiovascular, pulmonary, inflammatory, metabolic, low bone mass diseases, serotonin syndrome, and cancer.

BACKGROUND OF THE INVENTION

Two vertebrate isoforms of TPH, namely TPH1 and TPH2, have been identified. TPH1 is primarily expressed in the pineal gland and non-neuronal tissues, such as enterochromaffin (EC) cells located in the gastrointestinal (GI) tract. TPH2 (the dominant form in the brain) is expressed exclusively in neuronal cells, such as dorsal raphe or myenteric plexus cells. TPH catalyzes the hydroxylation of tryptophan in the biosynthesis of 5-HT. Thus, the pharmacological effects of 5-HT can be modulated by agents affecting TPH.

TPH1 inhibitors are known in the art. Spirocyclic compounds disclosed in U.S. Ser. No. 14/477,948, filed Sep. 5, 2014, can inhibit TPH1 and were found to reduce peripheral serotonin levels in animal models. The preparation of these compounds can include the coupling of an alcohol with a chloro-substituted heteroaromatic compound in the presence of base to yield an ether intermediate that can be used to make the final TPH1 inhibitor product. A particular chiral alcohol useful in the synthesis of TPH1 inhibitors is (R)-1-(5-chloro-[1,1'-biphenyl]-2-yl)-2,2,2-trifluoroethanol (see Formula A below). According to U.S. Ser. No. 14/477,948, this chiral alcohol is made by the coupling of phenyl boronic acid with (R)-1-(2-bromo-4-chlorophenyl)-2,2,2-trifluoroethanol. Alternative processes for the preparation of the compound of Formula A are provided herein.

SUMMARY OF THE INVENTION

The present invention provides processes for preparing (R)-1-(5-chloro-[1,1'-biphenyl]-2-yl)-2,2,2-trifluoroethanol (Formula A) and 1-(5-chloro-[1,1'-biphenyl]-2-yl)-2,2,2-trifluoroethanone (Formula B):

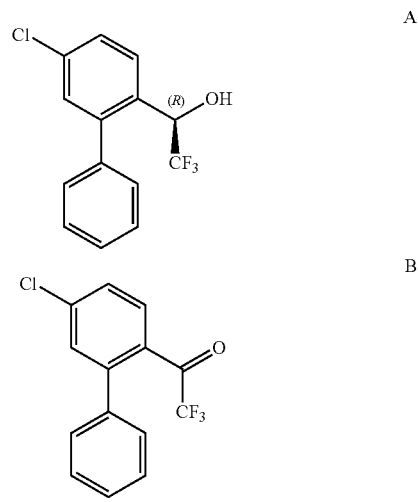

as described herein.

DETAILED DESCRIPTION

The present invention provides processes for preparing (R)-1-(5-chloro-[1,1'-biphenyl]-2-yl)-2,2,2-trifluoroethanol (Formula A) and 1-(5-chloro-[1,1'-biphenyl]-2-yl)-2,2,2-trifluoroethanone (Formula B) as set out, for example, in Scheme I, wherein X is selected from Br and I.

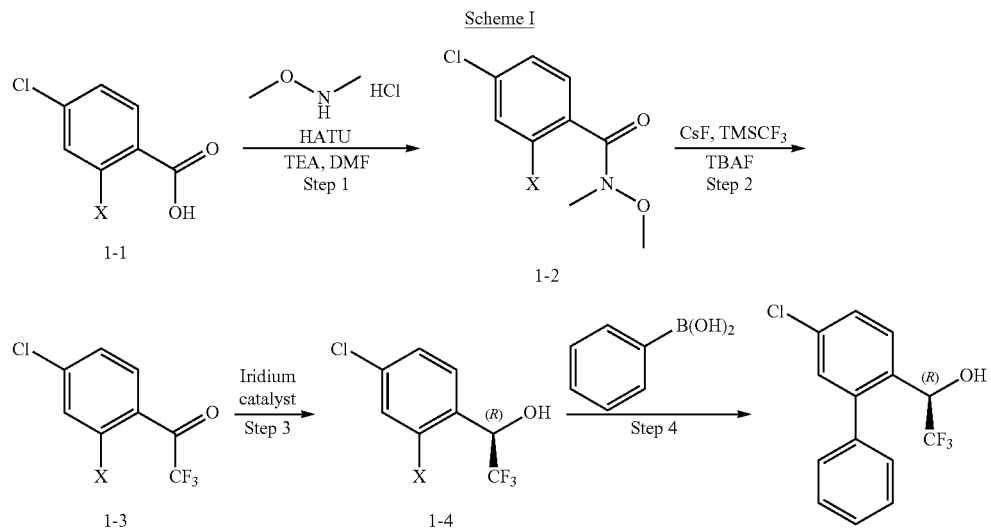

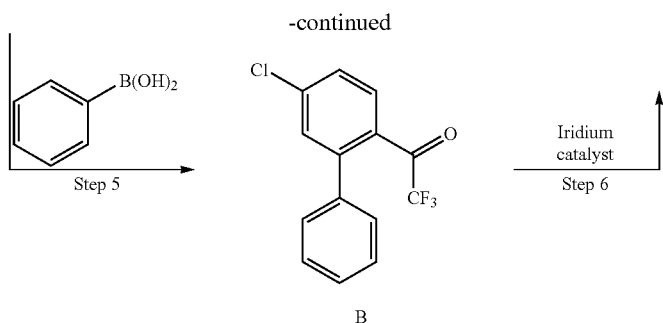

B

In some embodiments, the invention relates to a process for preparing a compound of Formula A:

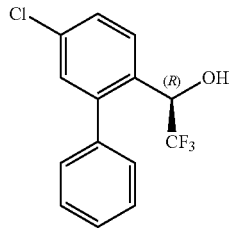

comprising, reacting a compound of Formula 1-4:

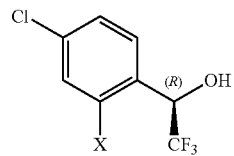

wherein X is selected from Br and I,
with phenylboronic acid to produce the compound of Formula A.

In some aspects of these embodiments, X is I. In other aspects of these embodiments, X is Br.

In some aspects of these embodiments, the reacting can be carried out under Suzuki coupling conditions such as in the presence of a Pd catalyst, for example, Pd$_2$(dppf)Cl$_2$. In further aspects of these embodiments, the reacting can be carried out in the presence of a solvent comprising, for example, dioxane and/or aqueous sodium carbonate. In further aspects of these embodiments, to facilitate the reacting, the coupling can be carried out at elevated temperature such as from 80 to 100° C. or at about 90° C.

In some embodiments, the compound of Formula 1-4:

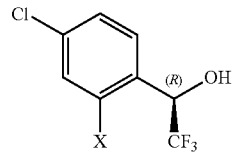

wherein X is selected from Br and I, is prepared by reducing a compound of Formula 1-3:

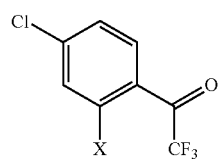

in the presence of a chiral catalyst.

In some aspects of these embodiments, X is I. In other aspects of these embodiments, X is Br.

In some aspects of these embodiments, the chiral catalyst comprises iridium such as the Ir catalyst that can be prepared by combining dichloro(pentamethylcyclopentadienyl)iridium(III) dimer with (1R,2R)-(−)-N-(4-toluenesulfonyl)-1,2-diphenylethylenediamine. In some aspects of these embodiments, the reduction is carried out at elevated temperature such as at about 30-50° C. or at about 40° C. In further aspects of these embodiments, the reduction is carried out in the presence of formate as a reductant. The formate can be in the form of salt such as a potassium salt or sodium salt. In further aspects of these embodiments, the reduction is carried out in the presence of a solvent which, for example, can comprise acetonitrile.

In some embodiments, the compound of Formula 1-3:

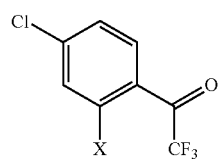

wherein X is selected from Br and I,
is prepared by combining a compound of Formula 1-2:

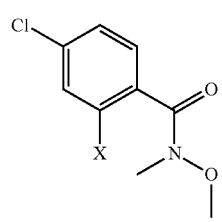

with trifluoromethyltrimethylsilane (TMSCF$_3$).

In some aspects of these embodiments, X is I. In other aspects of these embodiments, X is Br.

In some aspects of these embodiments, the combining is carried out in the presence of CsF. In further aspects of these embodiments, the combining is carried out at a reduced temperature such as at about −10 to 10° C., or at about 0° C. In further aspects of these embodiments, the combining is carried out in the presence of a solvent optionally comprising, for example, an aromatic solvent like toluene. In further aspects of these embodiments, the combining further comprises the step of adding tetra-n-butylammonium fluoride (TBAF), for example, after the compound of Formula 1-2 is combined with TMSCF$_3$.

In some embodiments, the compound of Formula 1-2:

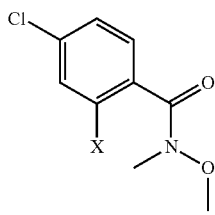

1-2 wherein X is selected from Br and I,
is prepared by coupling a compound of Formula 1-1:

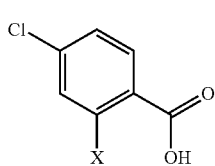

1-1 with N,O-dimethylhydroxylamine hydrochloride.

In some aspects of these embodiments, X is I. In other aspects of these embodiments, X is Br.

In some aspects of these embodiments, the coupling is carried out in the presence of a tertiary amine such as triethylamine (TEA). In further aspects of these embodiments, the coupling is carried out in the presence of a peptide coupling reagent such as (1-[bis(dimethylamino)methylene]-1H-1,2,3-triazolo[4,5-b]pyridinium 3-oxid hexafluorophosphate) (HATU). In further aspects of these embodiments, the coupling is carried out using oxalyl chloride. In further aspects of these embodiments, the coupling is carried out in the presence of a solvent optionally comprising, for example, dimethylformamide (DMF), or, for example, dichloromethane (CH$_2$Cl$_2$).

In some embodiments, the invention relates to a process for preparing a compound of Formula B:

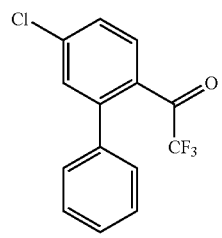

B wherein X is selected from Br and I, comprising reacting a compound of Formula 1-3:

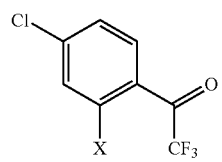

1-3 with phenylboronic acid to produce the compound of Formula B;

In some aspects of these embodiments, X is I. In other aspects of these embodiments, X is Br.

In some aspects of these embodiments, the reacting can be carried out under Suzuki coupling conditions such as in the presence of a Pd catalyst, for example, Pd$_2$(dppf)Cl$_2$. In further aspects of these embodiments, the reacting can be carried out in the presence of a solvent comprising, for example, dioxane and/or aqueous sodium carbonate. In further aspects of these embodiments, to facilitate the reacting, the coupling can be carried out at elevated temperature such as from 80 to 100° C. or at about 90° C.

In some embodiments, the invention relates to a process for preparing a compound of Formula A:

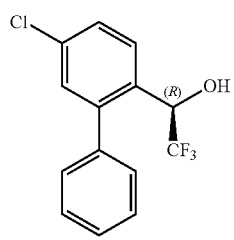

A comprising reducing a compound of Formula B:

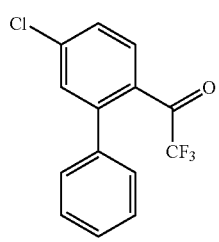

B in the presence of a chiral catalyst.

In some aspects of these embodiments, the chiral catalyst comprises iridium such as the Ir catalyst that can be prepared by combining dichloro(pentamethylcyclopentadienyl)iridium(III) dimer with (1R,2R)—(−)—N-(4-toluenesulfonyl)-1,2-diphenylethylenediamine. In further aspects of these embodiments, the reduction is carried out at elevated temperature such as at about 30-50° C. or at about 40° C. In further aspects of these embodiments, the reduction is carried out in the presence of formate as a reductant. The formate can be in the form of salt such as a potassium salt or sodium salt. In further aspects of these embodiments, the reduction is carried out in the presence of a solvent which, for example, can comprise acetonitrile.

In some embodiments, the present invention is directed to a compound of Formula A prepared by a process described herein.

In some embodiments, the invention is directed to a compound of Formula B:

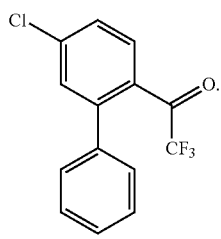

B

In some embodiments, the invention is directed to a compound of Formula B prepared by a process described herein.

In some embodiments, the invention is directed toward a compound of Formula 1-4:

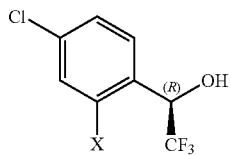

1-4 wherein X is selected from Br and I.

In some aspects of these embodiments, X is I. In other aspects of these embodiments, X is Br.

In some embodiments, the invention is directed to a compound of Formula 1-4 prepared by a process described herein.

In some embodiments, the invention is directed toward a compound of Formula 1-3:

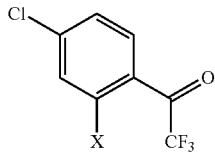

1-3 wherein X is selected from Br and I.

In some aspects of these embodiments, X is I. In other aspects of these embodiments, X is Br.

In some embodiments, the invention is directed to a compound of Formula 1-3 prepared by a process described herein.

In some embodiments, the invention is directed toward a compound of Formula 1-2:

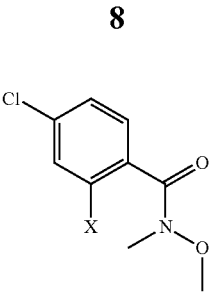

1-2 wherein X is selected from Br and I.

In some aspects of these embodiments, X is I. In other aspects of these embodiments, X is Br.

In some embodiments, the invention is directed to a compound of Formula 1-2 prepared by a process described herein.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination. While certain of the processes steps are illustrated in Scheme I above, it is intended that the individual process steps may be claimed individually or in any combination. It is not intended that the processes be limited to an overall process having each and every step depicted in Scheme I.

The term "compound," as used herein, is meant to include all stereoisomers, geometric isomers, tautomers, and isotopes of the structures depicted. Compounds herein identified by name or structure as one particular tautomeric form are intended to include other tautomeric forms unless otherwise specified. Compounds herein identified by name or structure without specifying the particular configuration of a stereocenter are meant to encompass all the possible configurations at the stereocenter. For example, if a particular stereocenter in a compound of the invention could be R or S, but the name or structure of the compound does not designate which it is, than the stereocenter can be either R or S.

The term "compound," as used herein, is further meant to include all isotopes of atoms occurring in the structures depicted. Isotopes include those atoms having the same atomic number but different mass numbers. For example, isotopes of hydrogen include tritium and deuterium.

In some embodiments, the compounds disclosed herein are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

As used herein, the phrase "elevated temperature" refers to a temperature higher than about room temperature (20-26° C.).

As used herein, the phrase "reduced temperature" refers to a temperature lower than about room temperature.

As used herein, the phrase "Suzuki coupling conditions" refers to reaction conditions that result in the formation of a carbon-carbon bond between aromatic moieties, one of which includes a halogen substituent and the other which includes a boronic acid or boronate substituent, where the reaction is carried out in the presence of a Pd(0) catalyst.

As used herein, the phrase "chiral catalyst" is a substance that pushes a reaction to favor one stereoisomer over another. In some embodiments, the chiral catalyst is a chiral coordination complex, such as a chiral coordination complex of iridium.

The present application also includes salts of the compounds described herein. In some embodiments, the salts are pharmaceutically acceptable salts which are conventional non-toxic salts of the parent compound formed, for example, from non-toxic inorganic or organic acids. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation; trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis*, 4th Ed., John Wiley & Sons: New York, 2006, which is incorporated herein by reference in its entirety.

The reactions of the processes described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the reaction step, suitable solvent(s) for that particular reaction step can be selected. Example solvents include water, alkanes (such as pentanes, hexanes, heptanes, cyclohexane, etc., or a mixture thereof), aromatic solvents (such as benzene, toluene, xylene, etc.), alcohols (such as methanol, ethanol, isopropanol, etc.), ethers (such as dialkylethers, methyl tert-butyl ether (MTBE), tetrahydrofuran (THF), dioxane, etc.), esters (such as ethyl acetate, butyl acetate, etc.), halogenated hydrocarbon solvents (such as dichloromethane (DCM), chloroform, dichloroethane, tetrachloroethane), dimethylformamide (DMF), dimethylsulfoxide (DMSO), acetone, acetonitrile (ACN), hexamethylphosphoramide (HMPA) and N-methyl pyrrolidone (NMP). Such solvents can be used in either their wet or anhydrous forms.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

$^1$H NMR Spectra were acquired on a Varian Mercury Plus 400 MHz spectrometer. For typical $^1$H NMR spectra, the pulse angle was 45 degrees, 8 scans were summed and the spectral width was 16 ppm (−2 ppm to 14 ppm). Typically, a total of about 32768 complex points were collected during the 5.1 second acquisition time, and the recycle delay was set to 1 second. Spectra were collected at 25° C. $^1$H NMR Spectra were typically processed with 0.3 Hz line broadening and zero-filling to about 131072 points prior to Fourier transformation. Chemical shifts were expressed in ppm relative to tetramethylsilane. The following abbreviations are used herein: br=broad signal, s=singlet, d=doublet, dd=double doublet, ddd=double double doublet, dt=double triplet, t=triplet, td=triple doublet, tt=triple triplet q=quartet, m=multiplet.

Liquid chromatography-mass spectrometry (LCMS) experiments to determine retention times and associated mass ions were performed using an Agilent Zorbax Bonus RP (reverse phase) column, 2.1×50 mm, 3.5 µm particle size, at a temperature of 50° C. and at a flow rate of 0.8 mL/min, 2 µL injection, mobile phase: (A) water with 0.1% formic acid and 1% acetonitrile, mobile phase (B) MeOH with 0.1% formic acid; retention time given in minutes. Method details: (I) ran on a Binary Pump G1312B with UV/Vis diode array detector G1315C and Agilent 6130 mass spectrometer in positive and negative ion electrospray mode with UV-detection at 220 and 254 nm with a gradient of 50-95% (B) in a 2.5 min linear gradient (II) hold for 0.5 min at 95% (B) (III) decrease from 95-5% (B) in a 0.1 min linear gradient (IV) hold for 0.29 min at 5% (B).

Example 1

Preparation of (R)-1-(5-chloro-[1,1'-biphenyl]-2-yl)-2,2,2-trifluoroethanol (Formula A)

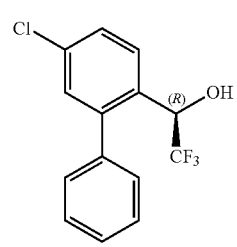

A

The compound of Formula A was prepared as described below (see also Scheme I above) using synthetic intermediates 1-1, 1-2, 1-3, and 1-4.

Step 1: 4-chloro-2-iodo-N-methoxy-N-methylbenzamide (1-2, X=I)

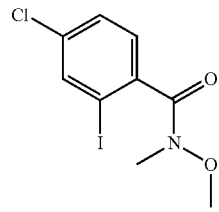

To a solution of 4-chloro-2-iodobenzoic acid (1-1, X=I) (CAS #:13421-13-1; Aldrich, SKU: 560146) (3 g, 10.62 mmol) and N,O-dimethylhydroxylamine hydrochloride (CAS #: 6638-79-5; Sigma Aldrich, SKU: D163708) (1.2 g, 12.31 mmol) in dimethylformamide (DMF) (30 mL), was added dropwise triethyl amine (TEA) (7.4 mL, 53.14 mmol), followed by the addition of (1-[bis(dimethylamino)methylene]-1H-1,2,3-triazolo[4,5-b]pyridinium 3-oxid hexafluorophosphate) (HATU) (6.1 g, 16.05 mmol). The reaction mixture was stirred at RT for 16 h and then diluted with $CH_2Cl_2$ and $H_2O$, and the aqueous layer was extracted with $CH_2Cl_2$ (4×20 mL). The combined organic layers were washed with brine, dried over $Na_2SO_4$, filtered, concentrated in vacuo and purified by silica gel chromatography (ethyl acetate/hexanes 1:4) to afford the title compound as a white solid (3.2 g. LCMS (MH+): 325.9. $^1$H NMR (400 MHz, $CDCl_3$-d): δ 3.11-3.38 (m, 3H), 3.47-3.90 (m, 3H), 7.20 (d, J=8 Hz, 1H), 7.37 (d, J=2 Hz, 1H), 7.84 (s, 1H).

Step 2: 1-(4-chloro-2-iodophenyl)-2,2,2-trifluoroethanone (1-3, X=I)

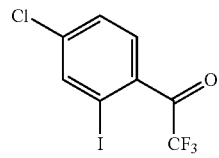 [SMILES: O=C(c1ccc(Cl)cc1I)C(F)(F)F]

To a solution of 4-chloro-2-iodo-N-methoxy-N-methylbenzamide (1-2, X=I) (Prepared in Step 1; 1.9 g, 5.84 mmol) and CsF (222 mg, 1.46 mmol) in toluene (5 mL), was added dropwise trifluoromethyltrimethylsilane (TMSCF$_3$) (2.2 mL, 14.88 mmol) at 0° C. The reaction mixture was then warmed to RT and stirred at that temperature for 20 h. Then, water (6 mL) and tetra-n-butylammonium fluoride (TBAF) (6 mL, 1 M in THF) were added to the reaction mixture, and the reaction mixture was heated to 50° C. for 2 h. The reaction mixture was then cooled to RT and extracted with ethyl acetate (3×20 mL). The combined organic layers were washed with brine, dried over $Na_2SO_4$, filtered, concentrated in vacuo and purified by silica gel chromatography (100% hexanes) to provide the title compound as a yellow oil (1.39 g). LCMS (MH+): 334.9. $^1$H NMR (400 MHz, $CDCl_3$-d): δ 7.51 (dd, J=10, 6 Hz, 1H), 7.37 (dd, J=10, 7 Hz, 1H), 7.84 (d, J=2 Hz, 1H).

Step 3: (R)-1-(4-chloro-2-iodophenyl)-2,2,2-trifluoroethanol (1-4)

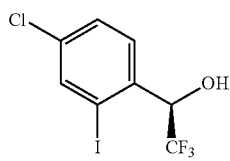 [SMILES: O[C@H](c1ccc(Cl)cc1I)C(F)(F)F]

To a solution of 1-(4-chloro-2-iodophenyl)-2,2,2-trifluoroethanone (1-3, X=I) (Prepared in Step 2; 4.0 g, 11.9 mmol) in $CH_3CN$ (20 mL) was added chiral iridium catalyst (20 mL of a 0.1 mM aqueous solution, prepared by mixing dichloro(pentamethylcyclopentadienyl)iridium(III) dimer (CAS #: 12354-84-6, 4.0 mg, 0.005 mmol) and (1R,2R)-(−)-N-(4-toluenesulfonyl)-1,2-diphenylethylenediamine (CAS #144222-34-4, Strem Chemicals catalogue #07-2371, 3.6 mg, 0.009 mmol) in water (40 mL) and heating the resultant mixture to 40° C. for 3 h). The reaction mixture was then charged with potassium formate (HCOOK) (5.03 g, 59.80 mmol), and heated at 40° C. for 12 h. Then the reaction mixture was cooled to RT and diluted with ethyl acetate and saturated aqueous solution of NaCl. Layers were separated and the aqueous layer was extracted with ethyl acetate (4×30 mL). The combined organic layers were washed with brine, dried over $Na_2SO_4$, filtered, and concentrated in vacuo to afford the title compound as a yellow solid (4.1 g, crude) that was used in the following steps without further purification. LCMS (MH+): 336.9. $^1$H NMR (400 MHz, $CDCl_3$-d): δ 3.5 (bs, 1H), 5.10 (dd, J=10 Hz, 6 Hz, 1H), 7.29 (dd, J=10, 6 Hz, 1H), 7.45 (dd, J=10, 7 Hz, 1H), 7.71 (d, J=2 Hz, 1H).

Confirmation of the (R) configuration was confirmed by Mosher Ester analysis. To a solution of (R)-1-(4-chloro-2-iodophenyl)-2,2,2-trifluoroethanol (50 mg, 0.15 mmol) in tetrahydrofuran (THF) (1 mL, anhydrous) was added 4-dimethylaminopyridine (23 mg, 0.19 mmol) and (R)-(−)-α-methoxy-α-(trifluoromethyl)phenylacetyl chloride (36 μL, 0.19 mmol). The resulting mixture was stirred at room temperature for 1 h then filtered. The filtrate was concentrated and purified by preparative thin layer chromatography (TLC) (ethyl actate:hexanes/1:40) to afford (R)—(R)-1-(4-chloro-2-iodophenyl)-2,2,2-trifluoroethyl 3,3,3-trifluoro-2-methoxy-2-phenylpropanoate (50 mg, 0.09 mmol, 98% e.e. which was confirmed by $^1$H NMR).

Step 4: (R)-1-(5-chloro-[1,1'-biphenyl]-2-yl)-2,2,2-trifluoroethanol (Formula A)

A solution of (R)-1-(4-chloro-2-iodophenyl)-2,2,2-trifluoroethanol (1-4) (3.1 g, 9.21 mmol), phenylboronic acid (CAS #: 98-80-6; Sigma Aldrich, SKU P20009) (1.2 g, 10.2 mmol), and Pd(dppf)Cl$_2$ (CAS #72287-26-4; Sigma Aldrich SKU: 697230) (337 mg, 0.46 mmol) in dioxane (30.0 mL) and $Na_2CO_3$ (10.0 mL, 2.0 M aqueous solution) was purged with $N_2$ three times, and the resultant reaction mixture was heated to 90° C. for 2 h. The reaction mixture was then cooled to RT and diluted with $CH_2Cl_2$ and water. Layers were separated and the aqueous layer was extracted with $CH_2Cl_2$ (3×50 mL). The combined organic layers were washed with brine, dried over $Na_2SO_4$, filtered, and purified by silica gel chromatography (ethyl actate/hexanes 1/10) to afford the title compound as a white solid (2.4 g over 2 steps). $^1$H NMR (400 MHz, CDCl$_3$-d): δ 3.51 (m, 1H), 5.08-5.13 (q, J=20, 7 Hz, 1H), 7.26-7.30 (m, 4H), 7.42-7.46 (m, 3H), 7.70 (d, J=8 Hz, 1H). The (R) configuration of the title product was confirmed by Mosher Ester analysis (98% e.e.) as described above for the product of Step 1: (R)-1-(4-chloro-2-iodophenyl)-2,2,2-trifluoroethanol.

Example 2

Preparation of 1-(5-chloro-[1,1'-biphenyl]-2-yl)-2,2,2-trifluoroethanone (Formula B)

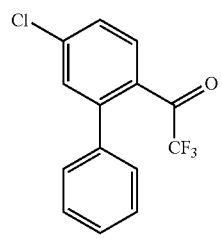

B

The compound of Formula B was prepared as described below (see also Scheme I above) using synthetic intermediates 1-1, 1-2, and 1-3.

Step 1:
4-chloro-2-iodo-N-methoxy-N-methylbenzamide (1-2, X=I)

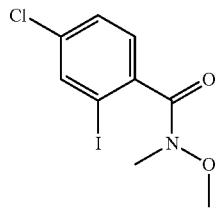

To a solution of 4-chloro-2-iodobenzoic acid (1-1, X=I) (296 g, 1.1 mol) in CH$_2$Cl$_2$ (3 L) and DMF (2 mL) was added oxalyl dichloride (266.1 g, 2.1 mol) dropwise at 0° C. over a period of 1 h. The resultant reaction mixture was stirred at 0° C. for 2 h and then concentrated in vacuo. The residue was dissolved in CH$_2$Cl$_2$ and concentrated twice. Then the residue was dissolved in CH$_2$Cl$_2$ (1 L) and cooled to 0° C., followed by the dropwise addition of a mixture of N,O-dimethylhydroxylamine hydrochloride (Sigma Aldrich, SKU: D163708; 112.4 g, 1.15 mol) in CH$_2$Cl$_2$ (1 L) and triethyl amine (1 L, 3.15 mol) at 0° C. over a period of 1 h. The reaction mixture was then warmed to RT and stirred at that temperature for 16 h. After this time, the mixture was diluted with H$_2$O and the aqueous layer was extracted with CH$_2$Cl$_2$. The combined organic layers were washed with brine, dried over Na$_2$SO$_4$, filtered, concentrated in vacuo and purified by silica gel chromatography (ethyl acetate/hexanes 1/4) to afford the title compound (320 g) as a white solid LCMS (MH+): 325.9. $^1$H NMR (400 MHz, CDCl$_3$-d): δ 3.11-3.38 (m, 3H), 3.47-3.90 (m, 3H), 7.20 (d, J=8 Hz, 1H), 7.37 (d, J=2 Hz, 1H), 7.84 (s, 1H).

Step 2: 1-(5-chloro-[1,1'-biphenyl]-2-yl)-2,2,2-trifluoroethanone (Formula B)

A solution of 1-(4-chloro-2-iodophenyl)-2,2,2-trifluoroethanone (1-3, X=I, prepared in Example 1, Step 2) (145 g, 0.43 mol), phenylboronic acid (CAS #: 98-80-6; Sigma Aldrich, SKU P20009; 55.5 g, 0.455 mol) and Pd(dppf)Cl$_2$ (CAS #72287-26-4; Sigma Aldrich SKU: 697230; 9.5 g, 0.013 mol) in dioxane (1450 mL) and Na$_2$CO$_3$ (435 mL, 2.0 M aqueous solution) was purged with Na and stirred at 90° C. for 2 h. After this time, the reaction mixture was cooled to RT and then diluted with H$_2$O. Layers were separated and the aqueous layer was extracted with ethyl acetate and the combined organic layers were washed with brine, dried over Na$_2$SO$_4$, filtered, concentrated in vacuo and purified by silica gel chromatography (100% hexanes) to afford the title compound (115 g) as a white solid. LCMS (MH+): 284.66. $^1$H NMR (400 MHz, CDCl$_3$-d): δ 7.23-7.27 (m, 2H), 7.42-7.44 (m, 3H), 7.47-7.49 (m, 2H), 7.67-7.70 (m, 1H)

Example 3

Preparation of (R)-1-(5-chloro-[1,1'-biphenyl]-2-yl)-2,2,2-trifluoroethanol (Formula A)

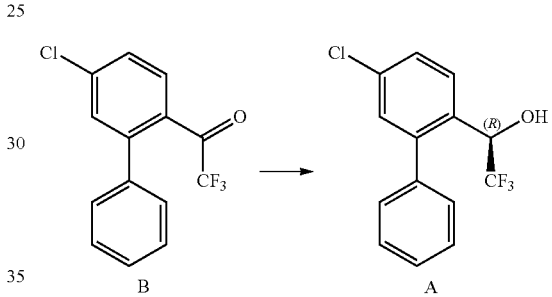

B        A

The compound of Formula A was prepared as described below (see also Scheme I above) using the compound of Formula B as synthetic starting material.

To a 22 L 3-necked reactor, fitted with a mechanical stirrer, a temperature probe, and a Na inlet, were charged sequentially dichloro(pentamethyl cyclopentadienyl)iridium (III) dimer ([Cp*IrCl2]2, 1.52 g, 1.90 mmol, CAS: 12354-84-6), (1R,2R)-(−)-(4-toluenesulfonyl)-1,2-diphenylethylenediamine (1.52 g, 4.15 mmol, CAS: 144222-34-4, Strem Chemicals catalogue #07-2371) and water (8 L) at RT. The resulting reaction mixture was heated to 40° C. for 3 h to provide a homogeneous orange solution. To this active catalyst solution at the current temperature (40° C.), was added potassium formate (1476 g, 17.55 mol), and a solution of 1-(2-phenyl-4-chlorophenyl)-2,2,2-trifluoroethanone (compound of Formula B prepared in Example 2) (1000 g, 3.51 mol) in CH$_3$CN (8 L). The reaction mixture was then stirred at 40° C. for 2 h and then cooled to RT and the layers were separated. The aqueous layer was extracted with MTBE (2×3 L) and the combined organic layers were dried over Na$_2$SO$_4$, filtered, and concentrated in vacuo to provide (R)-1-(2-phenyl-4-chlorophenyl)-2,2,2-trifluoroethanol (1006 g) as a thick yellow oil used without further purification.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A process for preparing a compound of Formula B:

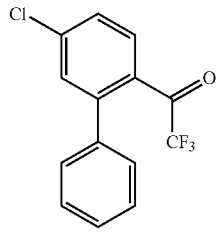

B comprising reacting a compound of Formula 1-3:

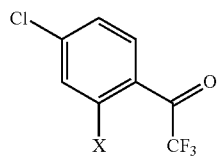

1-3 wherein X is selected from Br and I, with phenylboronic acid to produce the compound of Formula B.

2. The process of claim 1, wherein X is I.

3. The process of claim 1, wherein X is Br.

4. The process of claim 1, wherein said reacting is carried out under Suzuki coupling conditions.

5. The process of claim 1, wherein said reacting is carried out in the presence of a Pd catalyst.

6. The process of claim 5, wherein said Pd catalyst is $Pd_2(dppf)Cl_2$.

7. The process of claim 1, wherein said reacting is carried out in the presence of a solvent.

8. The process of claim 7, wherein said solvent comprises dioxane.

9. The process of claim 7, wherein said solvent comprises aqueous sodium carbonate.

10. The process of claim 1, wherein said reacting is carried out at elevated temperature.

11. The process of claim 10, wherein said elevated temperature is about 90° C.

* * * * *